United States Patent [19]

Rose et al.

[11] Patent Number: 4,756,716

[45] Date of Patent: Jul. 12, 1988

[54] PREPARATIONS CONTAINING SUBSTANTIVE NITRODIPHENYLAMINE DERIVATIVE HAIR DYES

[75] Inventors: David Rose, Hilden; Edgar Lieske, Duesseldorf; Norbert Maak, Nuess, all of Fed. Rep. of Germany

[73] Assignee: Henkel Kommanditgesellschaft auf Aktien, Duesseldorf, Fed. Rep. of Germany

[21] Appl. No.: 922,609

[22] Filed: Oct. 24, 1986

[30] Foreign Application Priority Data

Oct. 24, 1985 [DE] Fed. Rep. of Germany ....... 3537763

[51] Int. Cl.$^4$ .................... A61K 7/13; C07C 87/54
[52] U.S. Cl. .................................. 8/429; 8/405; 8/407; 8/409; 8/414; 260/505 C; 260/508; 562/435; 564/434
[58] Field of Search ............ 260/505 C, 508; 562/435; 564/434; 8/405, 407, 408, 409, 429, 414

[56] References Cited

U.S. PATENT DOCUMENTS

| | | | |
|---|---|---|---|
| 775,570 | 11/1904 | Laska | 564/433 |
| 2,687,431 | 8/1954 | Marschall | 260/509 |
| 3,930,792 | 1/1976 | Alperin et al. | 8/10.1 |

FOREIGN PATENT DOCUMENTS

| | | |
|---|---|---|
| 1569808 | 7/1970 | Fed. Rep. of Germany . |
| 2830497 | 1/1980 | Fed. Rep. of Germany . |
| 2216271 | 2/1973 | France . |
| 2360559 | 8/1977 | France . |
| 955743 | 4/1964 | United Kingdom ............... 564/434 |
| 1588215 | 4/1981 | United Kingdom . |

OTHER PUBLICATIONS

J. Prakt. Chem., (2), 91, pp. 205–206, 210–211, (1915).
Bell et al., Journal Society of Dye Chemists, vol. 82, (1966), pp. 410–414.
Chemical Abstracts, 72:110950d, p. 350.
Chemical Abstracts, 92:203416n, p. 321.
Chemical Abstracts, 88:89301m, p. 487.
Chemical Abstracts, 79:104940d, p. 400.
Beilsteins Handbuch der Organischen Chemie, F. Richter, Berlin, Germany, 1933, p. 564.
European Patent Office Search Report (RE: Ser. No. 922,609).
European Patent Office Search Report (RE: Ser. No. 922,610), date considered.

Primary Examiner—Paul Lieberman
Assistant Examiner—Linda D. Skaling
Attorney, Agent, or Firm—Ernest G. Szoke; Henry E. Millson, Jr.; Mark A. Greenfield

[57] ABSTRACT

Novel substituted nitrodiphenylamines and substantive hair dye preparations containing them or containing nitrodiphenylamines with different substituents. The dyes result in yellow to orange-red colored shades of high intensity and fastness and are more soluble in water than known nitroaniline dyes.

36 Claims, No Drawings

PREPARATIONS CONTAINING SUBSTANTIVE NITRODIPHENYLAMINE DERIVATIVE HAIR DYES

BACKGROUND OF THE INVENTION

1. Field of the Invention

This invention relates to hair-dyeing preparations containing substantive hair dyes.

2. Statement of Related Art

Hair-dyeing preparations of the type in question contain substantive hair dyes in a cosmetic carrier. In many cases, such hair-dyeing preparations additionally contain oxidation dye precursors or produce certain shades. The cosmetic carriers used for the substantive hair dyes and oxidation dye precursors, if any, are creams, emulsions, gels, shampoos, foam aerosols or other preparations suitable for application to the hair.

In addition to the oxidation dyes, which are formed by the oxidative coupling of one or more developer components with one another or with one or more coupler components, substantive hair dyes play a prominent part in the dyeing of hair. Substantive dyes have the advantage of being used without the addition of oxidizing agents. The substantive dyes used are predominantly nitrobenzene derivative compounds. They are used either on their own or in combination with other substantive dyes, such as anthraquinone dyes, indophenols, triphenylmethane dyes, cationic azo dyes, or with oxidation dyes.

Good hair-dyeing preparations have to form the required shades with sufficient intensity. They must be readily absorbed by human hair without excessively staining the scalp. The dye finishes produced by them must show high stability to light, heat, perspiration, shampoos and the chemicals used in the permanent waving of hair. Finally, they should be safe to use from the toxicological and dermatological viewpoint.

Among the substantive nitrobenzene derivatives, the nitroanilines and derivatives thereof play an important part because some of these dyes produce intensive, light-stable dye finishes. However, the known substantive nitroaniline dyes have disadvantages in that, on the one hand, they show only limited solubility in water, which leads to problems during formulation of the hair-dyeing preparations, and on the other hand are not sufficiently fast to washing, i.e. the dye finishes fade considerably after repeated washing. In addition, substantive dyes are required to show high compatibility with other dyes, for example with oxidation dye precursors and with the components normally used in oxidation hair-dyeing preparations because substantive dyes and oxidation dyes are often combined with one another for color modification. Accordingly, high stability to reducing agents and oxidizing agents is necessary.

DESCRIPTION OF THE INVENTION

Other than in the operating examples, or where otherwise indicated, all numbers expressing quantities of ingredients or reaction conditions used herein are to be understood as modified in all instances by the term "about".

It has been found that hair-dyeing preparations highly satisfying of the above requirements are those which contain as substantive hair dyes compounds corresponding to the following general formula

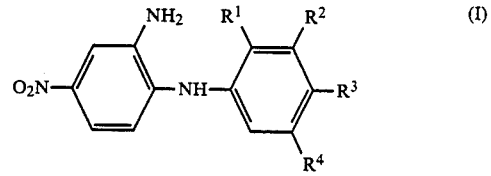

wherein:
(A) one of $R^1$ to $R^4$ is —SO$_3$H or —COOH and the remaining three, independently of one another, are hydrogen or a C$_{1-4}$-alkyl; or
(B) one of $R^1$ to $R^4$ is —SO$_3$H or —COOH, one of the remaining three is a C$_{1-4}$-alkoxy or chlorine, and the remaining two, independently of one another, are hydrogen or a C$_{1-4}$ alkyl;

and water-soluble salts thereof.

The dyes corresponding to general formula I produce yellow to orange-red shades of high intensity and high fastness to light and good resistance to leaching upon washing of the hair. In addition, they show better solubility in aqueous-alkaline medium than known nitroaniline dyes. The compounds corresponding to general formula I are dermatologically and toxicologically safe and are therefore particularly suitable for use in hair-dyeing preparations.

The hair-dyeing preparations according to the invention preferably contain those compounds of formula I, wherein:
(C) one of $R^1$ to $R^4$ is —SO$_3$H or —COOH and the remaining three are hydrogen; or
(D) one of $R^1$ to $R^4$ is —SO$_3$H or —COOH, one of the remaining three is methyl, methoxy, or chlorine, and the remaining two are hydrogen; or their water-soluble salts.

Particularly preferred substituents are:
at $R^1$: hydrogen, methyl, methoxy, or —COOH;
at $R^2$: hydrogen, methyl, —SO$_3$H, or —COOH;
at $R^3$: hydrogen, methyl, or —COOH; and
at $R^4$: hydrogen, chloro, or —COOH.

Compounds corresponding to general formula I, wherein $R^2$ or $R^3$ is —COOH and $R^1$ and $R^4$ are hydrogen, are known from the literature.

Compounds corresponding to formula I, wherein:
(E) one of $R^1$ to $R^4$ is —SO$_3$H and the remaining three are hydrogen; or
(F) one of $R^1$ to $R^4$ is —SO$_3$H or —COOH, one of the remaining three is methyl, methoxy, or chlorine, and the remaining two are hydrogen;

and their water soluble salts; are novel. Accordingly, the present invention also relates to these new compounds, per se.

In general, the compounds corresponding to general formula I are prepared by reaction of 2,4-dinitrofluorobenzene with an aniline derivative corresponding to the following formula

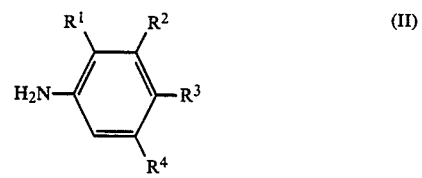

with elimination of HF in the presence of a base to form the corresponding dinitrodiphenylamine derivative corresponding to the following formula

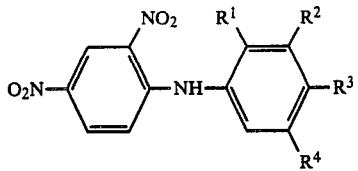

and reduction of this dinitrodiphenylamine derivative to the 2-amino-4-nitrodiphenylamine derivative of formula I. The substituents $R^1$ to $R^4$ in formulae II and III are the same as in formula I. The reduction of the 2,4-dinitrodiphenylamine derivative may be carried out particularly readily with a mixture of sodium sulfide and sulfur in aqueous-alcoholic solution.

In the context of the invention, the water-soluble salts are primarily understood to be the salts of strong bases, such as the alkali salts, for example sodium or potassium, or ammonium, $C_{2-4}$-alkanolammonium such as monoethanolammonium, triethanolammonium, or isopropanolammonium. The hair-dyeing preparations according to the invention may contain at least one of the substantive nitrodiphenylamine derivatives corresponding to general formula I either alone or in combination with known substantive dyes, for example with other nitrobenzene derivatives, anthraquinone dyes, triphenylmethane or azo dyes. In addition, the substantive dyes of general formula I, by virtue of their high resistance to reducing agents and oxidizing agents, are also eminently suitable for combination with oxidation dye precursors, i.e. for modifying the colors of oxidation hair dyes. Oxidation hair dyes contain as dye precursors developer components which form the oxidation dyes by oxidative coupling with one another or with suitable coupler components. The developer components used are primary aromatic amines containing another free or substituted hydroxy or amino group in the para or ortho position, diaminopyridine derivatives, heterocyclic hydrazones, 4-aminopyrazolone derivatives and 2,4,5,6-tetra-aminopyrimidine and derivatives thereof. The coupler components used are m-phenylenediamine derivatives, naphthols, resorcinol and resorcinol derivatives, pyrazolones and m-aminophenols.

To produce the hair-dyeing preparations according to the invention, the substantive hair dyes and the oxidation dye precursors, if any, are incorporated in a suitable cosmetic carrier, for example in creams, emulsions, gels, surfactant-containing foaming solutions such as shampoos, aerosol foams, or other preparations which are suitable for application to the hair, preferably with an aqueous base.

Standard ingredients of cosmetic preparations of this type include wetting agents and emulsifiers, such as anionic, nonionic or ampholytic surfactants, for example fatty alcohol sulfates, alkane sulfonates, α-olefin sulfonates, fatty alcohol polyglycolether sulfates, ethylene oxide adducts with fatty alcohols, fatty acids and alkylphenols, sorbitan fatty acid esters and fatty acid partial glycerides, fatty acid alkanolamides; thickeners such as methyl or hydroxyethyl cellulose, starch, fatty alcohols, paraffin oils, fatty acids, perfume oils and hair-care additives such as water-soluble cationic polymers, protein derivatives, pantothenic acid and cholesterol. The constituents of the cosmetic carriers are used in the usual quantities for producing the hair-dyeing preparations according to the invention; for example, emulsifiers are used in concentrations of from 0.5 to 30% by weight and thickeners in concentrations of from 0.1 to 25% by weight, based on the preparation as a whole.

The substantive dyes corresponding to general formula I are used in the hair-dyeing preparations according to the invention in a quantity of from 0.01 to 5.0% by weight and preferably in a quantity of from 0.1 to 2% by weight, based on the hair-dyeing preparation as a whole. Substantive hair dyes other than those of formula I may optionally be present in a total quantity of 0 to 5%, preferably 0.01 to 5%, all by weight based upon the preparation as a whole. In addition, known oxidation hair dye precursors (developers and couplers) may be present in a total quantity of 0 to 5%, preferably 0.01 to 5%, more preferably in a quantity of from 1 to 3% by weight, based on the total weight of the hair dye preparation.

Where the hair-dyeing preparation according to the invention contains oxidation dye precursors, it is advisable to add a small quantity of a reducing agent, for example from 0.5 to 2.0% by weight of sodium sulfite, to stabilize the oxidation dye precursors. In this case, an ozidizing agent is added to the hair-dyeing preparation before use in order to initiate oxidative development of the oxidation dye precursors. Suitable oxidizing agents are, in particular, hydrogen peroxide or adducts thereof with urea, melamine or sodium borate and also mixtures of these hydrogen peroxide adducts with potassium peroxydisulfate.

The hair dye preparations according to the invention may be used in a mildly acidic, neutral or alkaline medium, irrespective of the type of cosmetic preparation used, such as a cream, gel or shampoo. The hair dye preparations are preferably in the pH-range from 8 to 10. They may be used at temperatures of from 15° C. to 40° C. After a contact time of around 30 minutes, the hair-dyeing preparation is removed by rinsing from the hair to be dyed. The hair is then washed with a mild shampoo and dried. Washing with a shampoo is unnecessary when a carrier of high surfactant content, for example a dye shampoo, is used.

Hair dye finishes of high intensity and good fastness properties, particularly to washing, and high stability to bleeding and changes in color during shampooing may be obtained with the hair-dyeing preparations according to the invention. The following Examples are intended to illustrate the invention without limiting it in any way.

EXAMPLES

Production Examples

1.

2-amino-4-nitro-2'-methyldiphenylamine-5'-carboxylic acid

Step 1:

2,4-dinitro-2'-methyldiphenylamine-5'-carboxylic acid, Na salt 9.4 g 2,4-dinitrofluorobenzene were added dropwise to a mixture of 7.7 g 3-amino-4-methylbenzoic acid and 6 g sodium carbonate in a mixture of ethanol and water (1:1 parts by volume). The reaction mixture was heated to 70° C. and, after a reaction time of 1 hour, at 70° C., was cooled to 20° C. The deposit formed was filtered off and dried at 60° C. in a vacuum drying cabinet. Orange crystals melting at 187° C. were obtained.

Step 2:

A mixture of 2.75 g Na$_2$S.3H$_2$O and 1.34 g sulfur in a mixture of 2 ml water and 0.7 ml ethanol was added to a mixture of 7.5 g of the product of step 1 and 0.8 g sodium hydroxide in 300 ml of a mixture of ethanol and water (1:2 parts by volume). The reaction mixture was heated until it boiled under reflux and, after a reaction time of 3 hours, was cooled to 20° C., filtered off from undissolved fractions and approx. 60 ml solvent distilled off from the filtrate. The filtrate was then neutralized (to pH 7) by addition of concentrated hydrochloric acid and the deposit formed was filtered off and recrystallized from ethanol. An olive-colored powder melting at 229° to 238° C. was obtained.

The following compounds 2 to 7 were prepared as in Example 1:

2.

2-amino-4-nitro-2'-methoxydiphenylamine-5'-carboxylic acid

Starting product: 3-amino-4-methoxybenzoic acid
Step 1:
2,4-dinitro-2'-methoxydiphenylamine-5'-carboxylic acid, Na salt
Orange-red crystals, melting point above 250° C.
Step 2:
Orange powder, melting point 242° C.

3.

2-amino-4-nitro-4'-methyldiphenylamine-2'-carboxylic acid

Starting Product: 2-amino-5-methylbenzoic acid
Step 1:
2,4-dinitro-4'-methyldiphenylamine-2'-carboxylic acid, Na salt
Red powder, melting point above 250° C.
Step 2:
Brown powder, melting point above 250° C.

4.

2-amino-4-nitro-5'-chlorodiphenylamine-2'-carboxylic acid

Starting product 2-amino-4-chlorobenzoic acid
Step 1:
2,4-dinitro-5'-chlorodiphenylamine-2'-carboxylic acid, Na salt
Red powder, melting above 250° C.
Step 2:
Green powder, melting point above 250° C.

5.

2-amino-4-nitro-3'-methyldiphenylamine-2'-carboxylic acid

Starting product: 2-amino-6-methylbenzoic acid
Step 1:
2,4-dinitro-3'-methyldiphenylamine-2'-carboxylic acid, Na salt
Red powder, melting point above 250° C.
Step 2:
Red crystals
IR-spectrum (KBr, cm$^{-1}$): 1610, 1580, 1540, 1480, 1465, 1435, 1395, 1370, 1300, 1225, 1150, 1110, 1080, 960, 850, 810.

6. 2-amino-4-nitro-4'-methyldiphenylamine-3'-sulfonic acid

Starting product: 6-amino-m-toluene sulfonic acid
Step 1:
2,4-dinitro-4'-methyldiphenylamine-2'-sulfonic acid, Na salt
Orange crystals, melting point above 250° C.
Step 2:
Dark red crystals, melting point above 250° C.

7. 2-amino-4-nitrodiphenylamine-3'-sulfonic acid

Starting product: m-sulfanilic acid
Step 1:
2,4-dinitrodiphenylamine-3'-sulfonic acid, Na salt
Orange crystals, melting point 195° to 207° C. (with decomposition)
Step 2:
Olive-green powder, melting point 189° to 194° C.

The following compounds known from the literature were additionally included in the hair-dyeing tests:

8. 2-amino-4-nitrodiphenylamine-4'-carboxylic acid (J. Prakt. Chem. (2) 91, 205)

9. 2-amino-4-nitrodiphenylamine-3'-carboxylic acid (J. Prakt. Chem. (2) 91, 210)

Hair-dyeing tests

Hair-dyeing creams were prepared from the following constituents:

| | |
|---|---|
| C$_{12-18}$ fatty alcohol | 10 g |
| C$_{12-14}$ fatty alcohol + 2 E.O. sulfate, Na salt (28%) | 25 g |
| Water | 60 g |
| Substantive dye | 1 g |
| Ammonium sulfate | 1 g |
| Concentrated ammonium solution | to pH = 9.5 |
| Water q.s. ad | 100 g |

The constitutents were mixed together in the above order. After addition of the substantive dyes, the emulsion was first adjusted to pH 9.5 with concentrated ammonia solution and then made up with water to 100 g.

The dye cream was applied to about 5 cm long strands of standardized, 90% gray, but not specially pretreated human hair and left thereon for 30 minutes at 27° C. After dyeing, the hair was rinsed, washed with a standard shampoo and then dried.

The compounds of Examples 1 to 9 were used as substantive dyes.

The results of the dyeing tests are shown in Table I below.

TABLE I

| Substantive dye of Example No. | Color of the dyed hair |
|---|---|
| 1 | straw yellow |
| 2 | mandarin yellow |
| 3 | topaz yellow |
| 4 | ash blonde |
| 5 | wheat gold |
| 6 | light orange |
| 7 | orange |
| 8 | butter yellow |
| 9 | mandarin orange |

We claim:

1. A hair dyeing preparation comprising a cosmetic carrier, an anionic, nonionic or ampholytic surfactant present in an effective amount as a wetting agent and emulsifier, oxidation hair dye precursors present in a total quantity of 0 to 5% by weight, a first substantive hair dye present in a quantity of about 0.01–5.0% by weight, and a second substantive hair dye other than said first substantive hair dye present in 0 to 5% by weight, all percentages based upon the total weight of the preparation, said first substantive hair dye consisting essentially of at least one nitrodiphenylamine compound of the formula:

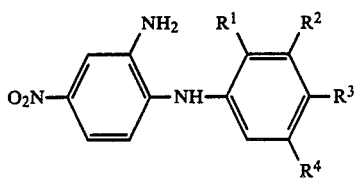

wherein:
(A) one of $R^1$ to $R^4$ is —$SO_3H$ or —COOH and the remaining three, independently of one another, are hydrogen or a $C_{1-4}$-alkyl; or
(B) one of $R^1$ to $R^4$ is —$SO_3H$ or —COOH, one of the remaining three is a $C_{1-4}$-alkoxy or chlorine, and the remaining two, independently of one another, are hydrogen or a $C_{1-4}$ alkyl;
and water-soluble salts thereof.

2. The preparation of claim 1 wherein substituents $R^1$ to $R^4$ are according to (A).

3. The preparation of claim 1 wherein substituents $R^1$ to $R^4$ are according to (B).

4. The preparation of claim 1 wherein said nitrodiphenylamine compound is in the form of a salt of sodium, potassium, ammonium, or a $C_{2-4}$-alkanolammonium.

5. The preparation of claim 1 wherein the nitrodiphenylamine compound substituents are:
(C) one of $R^1$ to $R^4$ is —$SO_3H$ or —COOH and the remaining three are hydrogen; or
(D) one of $R^1$ to $R^4$ is —$SO_3H$ or —COOH, one of the remaining three is methyl, methoxy, or chlorine, and the remaining two are hydrogen.

6. The preparation of claim 5 wherein substituents $R^1$ to $R^4$ are according to (C).

7. The preparation of claim 5 wherein substituents $R^1$ to $R^4$ are according to (D).

8. The preparation of claim 1 wherein
$R^1$ is: hydrogen, methoxy, or —COOH;
$R^2$ is: hydrogen, methyl, —$SO_3H$, or —COOH;
$R^3$ is: hydrogen, methyl, or —COOH; and
$R^4$ is: hydrogen, chlorine, or —COOH.

9. The preparation of claim 1 wherein said nitrodiphenylamine compound is:
2-amino-4-nitro-2'-methyldiphenylamine-5'-carboxylic acid.

10. The preparation of claim 1 wherein said nitrodiphenylamine compound is:
2-amino-4-nitro-2'-methoxydiphenylamine-5'-carboxylic acid.

11. The preparation of claim 1 wherein said nitrodiphenylamine compound is:
2-amino-4-nitro-4'-methyldiphenylamine-2'-carboxylic acid.

12. The preparation of claim 1 wherein said nitrodiphenylamine compound is:
2-amino-4-nitro-5'-chlorodiphenylamine-2'-carboxylic acid.

13. The preparation of claim 1 wherein said nitrodiphenylamine compound is:
2-amino-4-nitro-3'-methyldiphenylamine-2'-carboxylic acid.

14. The preparation of claim 1 wherein said nitrodiphenylamine compound is:
2-amino-4-nitro-4'-methyldiphenylamine-3'-sulfonic acid.

15. The preparation of claim 1 wherein said nitrodiphenylamine compound is:
2-amino-4-nitrodiphenylamine-3'-sulfonic acid.

16. The preparation of claim 1 wherein said nitrodiphenylamine compound is:
2-amino-4-nitrodiphenylamine-4'-carboxylic acid.

17. The preparation of claim 1 wherein said nitrodiphenylamine compound is:
2-amino-4-nitrodiphenylamine-3'-carboxylic acid.

18. A method for using the preparation of claim 1, comprising applying it to hair in a hair-coloring effective amount, permitting it to remain on said hair until color is imparted, and then rinsing said hair with water.

19. A method for using the preparation of claim 5, comprising applying it to hair in a hair-coloring effective amount, permitting it to remain on said hair until color is imparted, and then rinsing said hair with water.

20. A nitrodiphenylamine compound of the formula

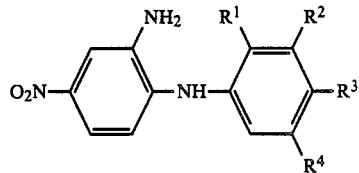

wherein:
(E) one of $R^1$ to $R^4$ is —$SO_3H$ and the remaining three are hydrogen; or
(F) one of $R^1$ to $R^4$ is —$SO_3H$ or —COOH, one of the remaining three is methyl, methoxy, or chlorine, and the remaining two are hydrogen; or a water-soluble salt thereof.

21. A hair dyeing preparation comprising a cosmetic carrier, oxidation hair dye precursors present in a total quantity of 0 to 5% by weight, a first substantive hair dye present in a quantity of about 0.01–5.0% by weight, and a second substantive hair dye other than said first substantive hair dye present in about 0.01 to 5% by weight, all percentages based upon the total weight of the preparation, said first substantive hair dye consisting essentially of at least one nitrodiphenylamine compound of the formula:

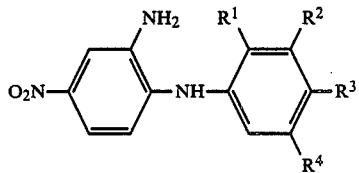

wherein:
(A) one of $R^1$ to $R^4$ is —$SO_3H$ or —COOH and the remaining three, independently of one another, are hydrogen or a $C_{1-4}$-alkyl; or (B) one of $R^1$ to $R^4$ is —$SO_3H$ or —COOH, one of the remaining three is a $C_{1-4}$-alkoxy or chlorine, and the remaining two, independently of one another, are hydrogen or a $C_{1-4}$ alkyl; and water-soluble salts thereof.

22. The preparation of claim 21 wherein substituents $R^1$ to $R^4$ are according to (A).

23. The preparation of claim 21 wherein substituents $R^1$ to $R^4$ are according to (B).

24. The preparation of claim 21 wherein said nitrodiphenylamine compound is in the form of a salt of sodium, potassium, ammonium, or a $C_{2-4}$-alkanolammonium.

25. The preparation of claim 21 wherein the nitrodiphenylamine compound substituents are:
(C) one of $R^1$ to $R^4$ is —$SO_3H$ or —COOH and the remaining three are hydrogen; or
(D) one of $R^1$ to $R^4$ is —$SO_3H$ or —COOH, one of the remaining three is methyl, methoxy, or chlorine, and the remaining two are hydrogen.

26. The preparation of claim 25 wherein substituents $R^1$ to $R^4$ are according to (C).

27. The preparation of claim 25 wherein substituents $R^1$ to $R^4$ are according to (D).

28. The preparation of claim 21 wherein
$R^1$ is: hydrogen, methyl, methoxy, or —COOH;
$R^2$ is: hydrogen, methyl, —$SO_3H$, or —COOH;
$R^3$ is: hydrogen, methyl, or —COOH; and
$R^4$ is: hydrogen, chlorine, or —COOH.

29. A hair dyeing preparation comprising a cosmetic carrier, oxidation hair dye precursors present in a total quantity of 0.01 to 5% by weight, a first substantive hair dye present in a quantity of about 0.01–5.0% by weight, and a second substantive hair dye other than said first substantive hair dye present in 0 to 5% by weight, all percentages based upon the total weight of the preparation, said first substantive hair dye consisting essentially of at least one nitrodiphenylamine compound of the formula:

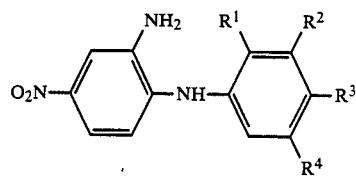

wherein:
(A) one of $R^1$ to $R^4$ is —$SO_3H$ or —COOH and the remaining three, independently of one another, are hydrogen or a $C_{1-4}$-alkyl; or
(B) one of $R^1$ to $R^4$ is —$SO_3H$ or —COOH, one of the remaining three is a $C_{1-4}$-alkoxy or chlorine, and the remaining two, independently of one another, are hydrogen or a $C_{1-4}$alkyl; and water-soluble salts thereof.

30. The preparation of claim 29 wherein substituents $R^1$ to $R^4$ are according to (A).

31. The preparation of claim 29 wherein substituents $R^1$ to $R^4$ are according to (B).

32. The preparation of claim 29 wherein said nitrodiphenylamine compound is in the form of a salt of sodium, potassium, ammonium, or a $C_{2-4}$-alkanolammonium.

33. The preparation of claim 29 wherein the nitrodiphenylamine compound substituents are:
(C) one of $R^1$ to $R^4$ is —$SO_3H$ or —COOH and the remaining three are hydrogen; or
(D) one of $R^1$ to $R^4$ is —$SO_3H$ or —COOH, one of the remaining three is methyl, methoxy, or chlorine, and the remaining two are hydrogen.

34. The preparation of claim 33 wherein substituents $R^1$ to $R^4$ are according to (C).

35. The preparation of claim 33 wherein substituents $R^1$ to $R^4$ are according to (D).

36. The preparation of claim 29 wherein
$R^1$ is: hydrogen, methyl, methoxy, or —COOH;
$R^2$ is: hydrogen, methyl, —$SO_3H$, or —COOH;
$R^3$ is: hydrogen, methyl, or —COOH; and
$R^4$ is: hydrogen, chlorine, or —COOH.

* * * * *